(12) United States Patent
Tolcher et al.

(10) Patent No.: US 10,022,421 B2
(45) Date of Patent: *Jul. 17, 2018

(54) TREATMENT OF PRIMARY AND METASTATIC CARCINOMA

(71) Applicant: Spectrum Pharmaceuticals Inc., Henderson, NV (US)

(72) Inventors: Anthony W. Tolcher, Shavano park, TX (US); Luigi Lenaz, Newton, PA (US)

(73) Assignee: Spectrum Pharmaceuticals, Inc., Henderson, NV (US)

( * ) Notice: Subject to any disclaimer, the term of this patent is extended or adjusted under 35 U.S.C. 154(b) by 66 days.

This patent is subject to a terminal disclaimer.

(21) Appl. No.: 15/061,821

(22) Filed: Mar. 4, 2016

(65) Prior Publication Data

US 2016/0287660 A1 Oct. 6, 2016

Related U.S. Application Data (63) Continuation of application No. 13/890,938, filed on May 9, 2013, now Pat. No. 9,308,235.

(60) Provisional application No. 61/644,704, filed on May 9, 2012.

(51) Int. Cl.
*A61K 38/00* (2006.01)
*A61K 38/10* (2006.01)
*A61K 31/337* (2006.01)

(52) U.S. Cl.
CPC ............ *A61K 38/10* (2013.01); *A61K 31/337* (2013.01)

(58) Field of Classification Search
None
See application file for complete search history.

(56) References Cited

U.S. PATENT DOCUMENTS

| | | | |
|---|---|---|---|
| 5,112,954 A | 5/1992 | Abrams | |
| 5,550,110 A | 8/1996 | Cody et al. | |
| 5,612,359 A | 3/1997 | Murugesan | |
| 5,811,416 A | 9/1998 | Chwalisz et al. | |
| 6,333,348 B1 | 12/2001 | Vogel et al. | |
| 6,469,058 B1 | 10/2002 | Grove et al. | |
| 7,976,835 B2 | 7/2011 | Gulati | |
| 8,026,216 B2 | 9/2011 | Gulati | |
| 8,030,278 B2 | 10/2011 | Gulati | |
| 8,217,010 B2 | 7/2012 | Gulati | |
| 8,349,802 B2 | 1/2013 | Gulati | |
| 8,394,757 B2 | 3/2013 | Gulati | |
| 8,440,620 B2 | 5/2013 | Gulati | |
| 8,642,026 B2 | 2/2014 | Gulati et al. | |
| 8,703,709 B2 | 4/2014 | Gulati | |
| 8,729,023 B2 | 5/2014 | Gulati et al. | |
| 8,957,014 B2 | 2/2015 | Gulati | |
| 9,308,235 B2 | 4/2016 | Tolcher et al. | |
| 2002/0082285 A1 | 6/2002 | Lebwohl | |
| 2003/0104976 A1 | 6/2003 | Davar et al. | |
| 2003/0229004 A1 | 12/2003 | Zarling et al. | |
| 2004/0138121 A1 | 7/2004 | Gulati | |
| 2006/0257362 A1* | 11/2006 | Gulati | A61K 31/00 424/85.2 |
| 2007/0032422 A1 | 2/2007 | Gulati | |
| 2008/0253994 A1* | 10/2008 | Gulati | A61K 31/282 424/85.2 |
| 2009/0155206 A1* | 6/2009 | Gulati | A61K 31/282 424/85.2 |

FOREIGN PATENT DOCUMENTS

| | | |
|---|---|---|
| EP | 655463 A1 | 5/1995 |
| EP | 815870 A2 | 1/1998 |
| EP | 950418 A2 | 10/1999 |
| WO | 1996/019233 A2 | 6/1996 |
| WO | 2000/067024 A1 | 11/2000 |
| WO | 2001/000198 A2 | 1/2001 |
| WO | 2001/091736 A2 | 12/2001 |
| WO | 2003/009805 A2 | 2/2003 |
| WO | 2003/045434 A2 | 6/2003 |
| WO | 2003/070234 A1 | 8/2003 |
| WO | 2004/037235 A2 | 5/2004 |
| WO | 2006/057988 A2 | 6/2006 |
| WO | 2006/091767 A2 | 8/2006 |

OTHER PUBLICATIONS

Battistini et al., Endothelins: A quantum leap forward. Drug News and Perspectives, vol. 8, No. 6, pp. 365-391 (1995).
Bell et al., A comparative study of tumour blood flow in modification in two rat tumour systems using endothelin-1 and angiotensin II: Influence of tumour size on angiotensin II response. Int. J. Cancer, 67(5) 730-8 (1996).
Bell et al., Effect of endothelin-1 and sarafotoxin, S6c on blood flow in a rat tumor. J. Cardiovasc. Pharmacol., vol. 26, Suppl 3, p. S222-S225 (1995).
Bell et al., Modification of blood flow in the HSN tumor and normal tissues of the rat by the endothelin Etb receptor agonist, IRL 1620. Int. J. Cancer, vol. 80, No. 2, pp. 295-302 (1999).
Bell et al., Tumor blood flow modification by endothelin-related peptides in the rat HSN fibrosarcoma. British Journal of Cancer, 74, Suppl. 27, pp. S161-S163 (1996).
Bell et al., Vascular response of tumor and normal tissues to Endothelin-1 following antagonism of Eta and Etb receptors in anaesthtised rats. Int. J. Cancer, vol. 73, No. 2, pp. 283-289 (1997).
Bhalla et al., Potentiation of morphine analgesia by BQ123, an endothelin antagonist. Peptides, vol. 23, pp. 1837-1845 (2002).

(Continued)

*Primary Examiner* — Sheela J. Huff
(74) *Attorney, Agent, or Firm* — K&L Gates LLP; Louis C. Cullman; Hal Gibson (57) ABSTRACT

Disclosed are methods of treating a chemotherapy-resistant cancer, of treating a cholangiocarcinoma, of treating a metastatic carcinoma, and of treating a transition cell urothelial carcinoma by administering a therapeutically effective amount of an endothelin B ($ET_B$) receptor agonist and a chemotherapeutic agent to a subject afflicted with such a cancer.

11 Claims, 4 Drawing Sheets

(56) References Cited

OTHER PUBLICATIONS

Bhargava et al., Modification of brain and spinal cord dopamine D1 receptors labeled with [3H]SCH 23390 after morphine withdrawal from tolerant and physically dependent rats. The Journal of Pharmacology and Experimental Therapeutics, vol. 252, No. 3, pp. 901-907 (1990).
Calbiochem Catalog (1996/1997) p. 208.
Cemazar et al., The endothelin B (ETB) receptor agonist IRL 1620 is highly vasoconstrictive in two synergenic rat tumour lines: Potential for selective tumour blood flow modification. Bristish Journal of Cancer, vol. 93, No. 1, pp. 98-106 (2005).
Chaplin et al., Modification of tumor blood flow: current status and future directions. Seminars in Radiation Oncology, vol. 8, No. 3, pp. 151-163 (1998).
Davar et al., Behavioral signs of acute pain produced by application of endothelin-1 to rat sciatic nerve. NeuroReport, vol. 9, No. 10, pp. 2279-2283 (1998).
Davenport, International Union of Pharmacology. XXIX. Update on Endothelin receptor nomenclature. Pharmacological Revews, vol. 54, No. 2, pp. 219-226 (2002).
Del Bufalo et al., Endothelin-1 acts as a survival factor in ovarian carcinoma cells. Clinical Science, vol. 103, Suppl. 48, pp. 302S-305S (2002).
Duggan et al., Protection against aspirin-induced human gastric mucosal injury by bosentan, a new endothelin-1 receptor antagonist. Aliment Pharmacal. Ther., vol. 13, pp. 631-635 (1999).
Eisenberger, Chemotherapy in prostate cancer. Current Genitourinary Cancer Surgery, pp. 507-518 (1990).
Fabricio et al., Essential role for endothelin Etb receptors in fever induced by LPS (E. coli) in rats. British Journal of Pharmacology, vol. 125, pp. 542-548 (1998).
Filep et al., Effects of calcium antagonists on endothelin-1-induced myocardial ischaemia and oedema in the rat. British Journal of Pharmacol., vol. 118(4), pp. 893-900 (1996).
Gaidano et al., Lymphomas. Cancer Principles and Practice of Oncology, 5th Edition, 1997, p. 2198.
Griffin et al., Effect of a combination of mild-temperature hyperthermia and nicotinamide on the radiation response of experimental tumors. Radiation Research, vol. 153, No. 3, p. 327-331 (2000).
Hellman, Radiation Therapy. Cancer. Principles and Practice of Oncology, 5th Edition, 1997, p. 326.
Ishibashi et al., Growth of hepatocarcinoma and endothelian. Annual Research Report, Foundation for Growth Science, No. 19, p. 193-204 (1996).
Jarvis et al., ABT-627, an endothelin Eta receptor-selective antagonist, attenuates tactile allodynia in a diabetic rat model of neuropathic pain. European Journal of Pharmacology, vol. 388, pp. 29-35 (2000).
Jordan et al., Insulin increases the sensitivity of tumors to irradiation: involvement of an increase in tumor oxygenation mediated by nitric oxide-dependent decrease of the tumor cells oxygen consumption. Cancer Research, vol. 62, pp. 3555-3561 (2002).
Jordan et al., Potentiation of radiation-induced regrowth delay by isosorbide dinitrate in FSAII murine tumors. Int. J. Cancer, vol. 103, No. 1, pp. 138-141 (2003).
K. Parfitt (ED)., Analgesics Anti-inflammatory drugs and antipyretics. Martindale the complete drug reference (32nd Edition), Pharmaceutical Press, 1999.
Kikuchi et al., Decreased Etb receptor expression in human metastatic melanoma cells. Biochemical and Biophysical Research Communications, vol. 219, No. 3, pp. 734-739 (1996).
Kroodsma et al., Endothelins: possibly a new pharmacological starting point in cardiovascular disease, kidney disease and oncological conditions. Ned Tijdschr Geneeskd. vol. 141, No. 38, pp. 1806-1810 (1997).
Lahav et al., An endothelin receptor B antagonist inhibits growth and induces cell death in human melanoma cells in vitro and in vivo. Prcoeedings of the National Academy of Sciences of USA, vol. 96, pp. 11496-11500 (1999).
Lenaz et al., IRL-1620 increases the efficacy of radiation treatment in mice bearing lymphoma cell induced tumors. Blood, vol. 108 (11), Part 2, p. 269B (2006).
Martinive et al., Reversal of temporal and spatial heterogeneities in tumor perfusion identifies the tumor vascular tone as a tunable variable to improve drug delivery. Molecular Cancer Therapeutics, vol. 5 (6): 1620-1627 (2006).
Matsumaru et al., Bosentan, a novel synthetic mixed-type endothelin receptor antagonist, attenuates acute gastric mucosal lesions induced by indomethacin and HCI in the rat: Role of endogenous endothelin-1. Journal of Gastroenterology, vol. 32, pp. 164-170 (1997).
McQueen et al., Endothelin-1 activates ETA receptors to cause reflex scratching in BALB/c mice. British Journal of Pharmacoogy, 151, pp. 278-284 (2007).
Murata et al., Chronic vascular toxicity of doxorubicin in an organ-cultured artery. British Journal of Pharmacology, vol. 132, pp. 1365-1373 (2001).
Nelson et al., Endothelin-1 production and decreased endothelin B receptor expression in advanced prostate cancer. Cancer Research, vol. 56, No. 4, p. 663-668 (1996).
Nieder et al, The role of pentoxifylline as a modifier of radiation therapy. Cancer Treatment Reviews, vol. 31(6):148-455 (2005).
NTC00613691 downloaded from the web at clinicaltrials.gov on Dec. 18, 2011, A phase I, open-pabel, ascending dose study of the safety, tolerability, pharmacokinetics and pharmacodynamics of the endothelin B agonist, SPI-1620, in patients with recurrent or progressive carcinoma.
Paclitaxel (TAXOL) insert, revised Jan. 2008, Bristol-Meyers Squibb Company.
Rai et al., Etb receptor agonist, IRL 1620, does not affect paclitaxel plasma pharmacokinetics in breast tumour bearing rats. Journal of Pharmacy and Pharmacology, vol. 57, No. 7, pp. 869-879 (2005).
Rai, et al., Evidence for the involvement of ETB receptors in ET-1-induced changes in blood flow to the rat breast tumor. Cancer Chemother. Pharmacol., vol. 51, No. 1, p. 21-28 (2003).
Rajeshkumar et al., Endothelin B receptor agonist, IRL 1620, enhances the anti-tumor efficacy of paclitaxel in breast tumor rats. Breast Cancer Research and Treatment, vol. 94, No. 3, p. 237-247 (2005).
Rajeshkumar et al., ETB receptor agonist, IRL-1620 enhances the efficacy of cyclophosphamide and cisplatin in ovarian tumor bearing mice. Proceedings of the American Association for Cancer Research, vol. 48, p. 961 (2007).
Rajeshkumar et al., IRL-1620, a tumor selective vasodilator, augments the uptake and efficacy of chemotherapeutic agents in prostate tumor rats. The Prostate, 67: 701-713 (2007).
Rajeshkumar et al., N-Suc-[Glu9, Ala11,15]ET-1(8-21) Increases blood perfusion and enchances paclitaxel delivery to the tumor. Proceeding of the Annual meeting of the American Association for Cancer Research, vol. 46, p. 5741 (2005).
Rowinsky et al, Paclitaxel (Taxol). Review Article in the New England Journal of Medicine, vol. 332, No. 15, pp. 1004-1014 (1995).
Seo et al., The interaction between two radiosensitizers: 5-iododeoxyuridine and caffeine. Cancer Research, vol. 66, No. 1, pp. 490-498 (2006).
Sonveaux et al., "Modulation of the tumor vasculature functionality by ionizing radiation accounts for tumor radiosensitization and promotes gene delivery", The FASEB Journal, vol. 16, No. 14, p. 1979-1981 (2002).
Sonveaux et al., Endothelin-1 is a critcal mediator of myogenic tone in tumor arterioles: implications for cancer treatment. Cancer Research, vol. 64(9): 3209-3214 (2004).
Takai et al., A potent and specific agonist, Suc-[Glu9, Ala11,15]-Endothelin-1 (8-21), IRL 1620, for the ETB receptor. Biochemical and Biophysical Research Communications, vol. 184, No. 2, pp. 953-959 (1992).
Takita H., Effect of vasodilators in experimental solid tumor chemotherapy. Journal of Experimental and Clinical Cancer Research, vol. 2, No. 1, pp. 47-48 (1999).
TAXOL product label (Feb. 10, 2010).

(56) References Cited

OTHER PUBLICATIONS

University of Illinois at Chicago: List of Posters presentations in 2004 AAPS Annual Meeting (Baltimore), www2.uic.edu/std_orgs/prof/aaps/posters.htm, Online pp. 1-4.
Wu C., Recent discovery and development of endothelin receptor antagonists. Exp. Opin. Ther. Patents, 10(11), 1653-1668 (2000).
Wu-Wong et al., Extracellular signal-regulated kinases are involved in the antiapoptotic effect of endothelin-1. The Journal of Pharmacology and Experimental Therapeutics, vol. 293(2), pp. 514-521 (2000).
Tozer, Tumour Microcirculation, Gray Laboratory Cancer Research Trust Report (2000).

* cited by examiner

TREATMENT OF PRIMARY AND METASTATIC CARCINOMA

CROSS-REFERENCE TO RELATED APPLICATIONS

The present application is a continuation of U.S. patent application Ser. No. 13/890,938 filed on May 9, 2013, which claims the benefit under 35 U.S.C. § 119(e) to U.S. Provisional Application No. 61/644,704 filed May 9, 2012, the contents of which are incorporated herein by reference in their entirety.

FIELD OF THE INVENTION

The present disclosure relates to medicine, cancer, and more specifically, to the treatment of primary and metastatic carcinomas with combination therapies.

BACKGROUND

Successful treatment of cancer, including primary and metastatic solid tumors, remains an unfulfilled medical goal, despite increased understanding of the molecular biology of tumor cells and the availability of an increased number of potential therapeutic agents.

One problem in the treatment of cancers is that an effective dose of a wide variety of potential chemotherapeutic agents is restricted by the non-selective, highly toxic effect of these agents on normal tissues. As a result, many patients suffer from the side effects of chemotherapy without reaping the benefits of the treatment. A related problem is an often poor, and thus therapeutically-deficient, delivery of the chemotherapeutic drug specifically to the tumor. Thus, there is a necessity to develop more specific and less toxic cancer therapies.

Another problem is related to the identification of the cancer for proper treatment. Typically the cancerous tissue is examined under a microscope to determine the cell type, enabling a physician to determine if that type of cell is normally found in the part of the body from which the tissue sample was taken, or whether it is metastatic. The use of immunohistochemistry enables identification of many of these metastases. It is theorized that metastasis always coincides with a primary cancer, and, as such, is a tumor that started from a cancer cell or cells in another part of the body. However, over 10% of patients will have metastases without a primary tumor found. In these cases, the primary tumor as "unknown" or "occult," and the patient is said to have a cancer of unknown primary origin. It is estimated that 3% of all cancers are of unknown primary origin. This can be problematic because effective treatment of a cancer begins with its identification.

Although the cells in a metastatic tumor resemble those in the primary tumor, difficulties in treatment can arise because the metastatic cancer may have different characteristics than the primary cancer. Some cancers have been found to have a "metastatic signature", or differences in the expression of a subset of genes between the primary cancer and its metastasis. Accordingly, because of these genetic differences, a physician cannot assume that successful treatment of a primary cancer will be the same as treatment of a metastatic cancer, and vice versa. Thus there remains a need for effective treatments for both metastatic and primary cancers.

Further problems concern the treatment of inoperable cancers. Some of these inoperable cancers remain incurable by chemotherapy. For example, cholangiocarcinoma, a cancer of the bile ducts which drain bile from the liver into the small intestine, is considered to be an incurable and rapidly lethal disease unless all of its tumors can be fully resected. For non-resectable cases, the 5-year survival rate is 0% where the disease is inoperable because distal lymph nodes show metastases, and less than 5% in general. Overall median duration of survival is less than 6 months in inoperable, untreated, otherwise healthy patients with tumors involving the liver. A steady increase in the incidence of intrahepatic cholangiocarcinoma has been documented over the past several decades in North America, Europe, Asia, and Australia. Unfortunately, most patients have advanced and inoperable disease at the time of diagnosis. In these patients, their disease can be managed, though never cured, with chemotherapy and/or radiation therapy.

Similarly, transitional cell carcinoma (TCC, also termed urothelial cell carcinoma or UCC) is another problematic cancer to treat. TCC typically occurs in the urinary system, including the kidney, bladder, ureter, urethra, and/or urachus, and arises from the transition epithelium, a tissue lining the inner surface of these hollow organs. TCC is the most common tumor of the renal pelvis. Over 70,000 cases of bladder cancer are diagnosed annually in the United States. Upper urinary tract TCC is estimated to occur in 5% of all urothelial cancers and in less than 10% of renal tumors. Evidence indicates that the frequency of upper urinary tract malignancies is increasing. Treatment for limited stage TCC is surgical resection of the tumor, but reoccurrence is common due to the presence of occult micrometastases at diagnosis. While five-year survival rates in patients with invasion beyond muscle can approach 40 percent, survival for patients with lymph node involvement does not exceed 10 percent. Chemotherapy for TCC consisting of the "MVAC" regimen (methotrexate, vinblastine, adriamycin and cisplatin) has been used with limited success.

Thus, there remains a need for more effective chemotherapeutic treatment of metastatic carcinoma, and for cholangiocarcinoma and TCC, especially in cases of inoperable disease.

SUMMARY

Cholangiocarcinoma, transition cell urothelial carcinoma, and metastatic carcinomas can be treated with endothelin B ($ET_B$) receptor agonists in combination with a chemotherapeutic agent. The $ET_B$ receptor agonist targets $ET_B$ receptors in tumor vasculature to enhance tumor blood flow, which, in turn enhances the response of various chemotherapeutic agents in tumor bearing animals.

Generally described are methods of treating a cholangiocarcinoma, comprising: (a) administering a therapeutically effective amount of an $ET_B$ receptor agonist and a therapeutically effective amount of chemotherapeutic agent to a subject suffering from a cholangiocarcinoma; and (b) detecting a reduction in the size or in the growth of the cholangiocarcinoma. In some embodiments, the $ET_B$ receptor agonist is IRL-1620, and in certain embodiments, the therapeutically effective amount of IRL-1620 is about 5 $\mu g/m^2$ to about 11 $\mu g/m^2$, about 6 $\mu g/m^2$ to about 10 $\mu g/m^2$, about 7 $\mu g/m^2$ to about 9 $\mu g/m^2$, about 5 $\mu g/m^2$, about 6 $\mu g/m^2$, about 7 $\mu g/m^2$, about 8 $\mu g/m^2$, about 9 $\mu g/m^2$, about 10 $\mu g/m^2$, or about 11 $\mu g/m^2$. In some embodiments, the chemotherapeutic agent is docetaxel, and in particular embodiments, the therapeutically effective amount of docetaxel is about 60 mg/m² to about 75 mg/m², about 60 mg/m², about 65 mg/m², about 70 mg/m² or about 75 mg/m².

In some embodiments, the cholangiocarcinoma can be a metastatic cholangiocarcinoma. In certain embodiments, the $ET_B$ receptor agonist and the chemotherapeutic agent are administered simultaneously or are administered as a single composition. In other embodiments, the $ET_B$ receptor agonist and the chemotherapeutic agent are administered sequentially. For example, the $ET_B$ receptor agonist is administered prior to the chemotherapeutic agent. In some embodiments, the cholangiocarcinoma being treated is unresponsive to taxane chemotherapy.

In another aspect, the disclosure provides methods of treating a metastatic carcinoma, comprising: (a) administering a therapeutically effective amount of an $ET_B$ receptor agonist and a chemotherapeutic agent to a subject suffering from a metastatic carcinoma; and (b) detecting a reduction in the size or in the growth of the metastatic carcinoma. In some embodiments the $ET_B$ receptor agonist is IRL-1620, and in particular embodiments, the therapeutically effective amount of IRL-1620 is about 5 µg/m² to about 11 µg/m², about 6 µg/m² to about 10 µg/m², about 7 µg/m² to about 9 µg/m², about 5 µg/m², about 6 µg/m², about 7 µg/m², about 8 µg/m², about 9 µg/m², about 10 µg/m², or about 11 µg/m². In some embodiments, the chemotherapeutic agent is docetaxel, and in particular embodiments, the therapeutically effective amount of docetaxel is about 60 mg/m² to about 75 mg/m², about 60 mg/m², about 65 mg/m², about 70 mg/m² or about 75 mg/m². In certain embodiments, the metastatic carcinoma is a prostate cancer, an ovarian cancer, a breast cancer or a cholangiocarcinoma. In some embodiments, the $ET_B$ receptor agonist and the chemotherapeutic agent are administered substantially simultaneously or are administered as a single composition. In other embodiments, the ETB receptor agonist and the chemotherapeutic agent are administered sequentially, such as where the ETB receptor agonist is administered prior to the chemotherapeutic agent. In some embodiments, the cancer being treated is resistant to taxane chemotherapy.

In yet another aspect, the disclosure provides methods of treating a transition cell urothelial carcinoma, comprising: (a) administering a therapeutically effective amount of an $ET_B$ receptor agonist and a chemotherapeutic agent to a subject suffering from a transition cell urothelial carcinoma; and (b) detecting a reduction in the size or in the growth of the transition cell urothelial carcinoma. In some embodiments, the $ET_B$ receptor agonist is IRL-1620. In certain embodiments the therapeutically effective amount of IRL-1620 is about 5 µg/m² to about 11 µg/m², about 6 µg/m² to about 10 µg/m², about 7 µg/m² to about 9 µg/m², about 5 µg/m², about 6 µg/m², about 7 µg/m², about 8 µg/m², about 9 µg/m², about 10 µg/m², or about 11 µg/m². In some embodiments, the chemotherapeutic agent is docetaxel, and in particular embodiments, the therapeutically effective amount of docetaxel is about 60 mg/m² to about 75 mg/m², about 60 mg/m², about 65 mg/m², about 70 mg/m² or about 75 mg/m². In certain embodiments, the metastatic carcinoma is a prostate cancer, an ovarian cancer, a breast cancer or a cholangiocarcinoma. In some embodiments, the $ET_B$ receptor agonist and the chemotherapeutic agent are administered substantially simultaneously or are administered as a single composition. In other embodiments, the $ET_B$ receptor agonist and the chemotherapeutic agent are administered sequentially, such as where the $ET_B$ receptor agonist is administered prior to the chemotherapeutic agent. In some embodiments, the carcinoma being treated is resistant to taxane chemotherapy.

The disclosure also provides methods of treating a chemotherapy-resistant cancer, comprising: (a) administering a therapeutically effective amount of an $ET_B$ receptor agonist and a therapeutically effective amount of chemotherapeutic agent to a subject suffering from a chemotherapy-resistant cancer; and (b) detecting a reduction in the size or in the growth of the cancer. In some embodiments, the $ET_B$ receptor agonist is IRL-1620. In certain embodiments the therapeutically effective amount of IRL-1620 is about 5 µg/m² to about 11 µg/m², about 6 µg/m² to about 10 µg/m², about 7 µg/m² to about 9 µg/m², about 5 µg/m², about 6 µg/m², about 7 µg/m², about 8 µg/m², about 9 µg/m², about 10 µg/m², or about 11 µg/m². In some embodiments, the chemotherapeutic agent is docetaxel, and in particular embodiments, the therapeutically effective amount of docetaxel is about 60 mg/m² to about 75 mg/m², about 60 mg/m², about 65 mg/m², about 70 mg/m² or about 75 mg/m².

In certain embodiments, the chemotherapy-resistant cancer is a prostate cancer, an ovarian cancer, a breast cancer, or a cholangiocarcinoma. In some embodiments, the $ET_B$ receptor agonist and the chemotherapeutic agent are administered substantially simultaneously or are administered as a single composition. In other embodiments, the ETB receptor agonist and the chemotherapeutic agent are administered sequentially, such as where the ETB receptor agonist is administered prior to the chemotherapeutic agent.

BRIEF DESCRIPTION OF THE DRAWINGS

The foregoing and other objects of the present disclosure, the various features thereof, as well as the disclosure itself may be more fully understood from the following description, when read together with the accompanying drawings in which:

FIG. 1A shows the cholangiocarcinoma prior to chemotherapy with docetaxel and IRL-1620 and FIG. 1B shows the cholangiocarcinoma after about 12 weeks of chemotherapy with docetaxel and IRL 1620;

FIG. 2A shows the primary cholangiocarcinoma prior to chemotherapy with docetaxel and IRL-1620 showing solid tumors, and FIG. 2B shows the primary cholangiocarcinoma after about 9 weeks of chemotherapy with docetaxel and IRL-1620 showing a cavitation of the tumors;

FIG. 3A shows the TCC urothelium prior to chemotherapy with docetaxel and IRL-1620 showing solid tumors, and FIG. 3B shows the TCC urothelium after about 6 weeks of chemotherapy with docetaxel and IRL-1620 showing a cavitation of the tumors;

FIGS. 4 A and 4B are is a representations of a CT scan of a TCC urothelium in a patient unresponsive to previous treatment with a taxane-based drug. FIG. 4A shows the TCC urothelium prior to chemotherapy with docetaxel and IRL-1620 showing solid tumors, and FIG. 4B shows the TCC urothelium after about 6 weeks of chemotherapy with docetaxel and IRL-1620 showing a cavitation of the tumors.

DESCRIPTION

Figure 1A:
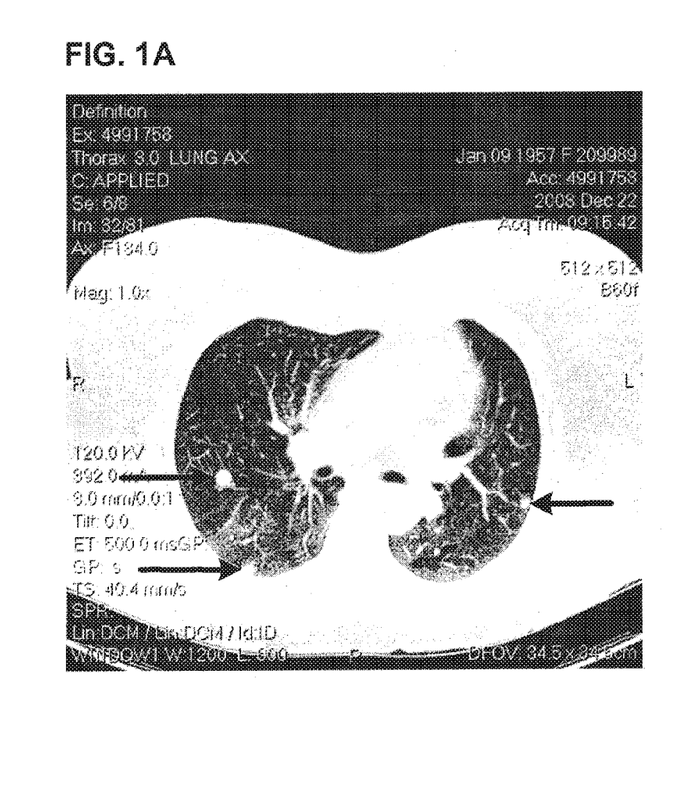
FIGS. 1A and 1B are representations of a CT scan of a cholangiocarcinoma in a patient unresponsive to previous treatment with a taxane-based drug.
Figure 1B:
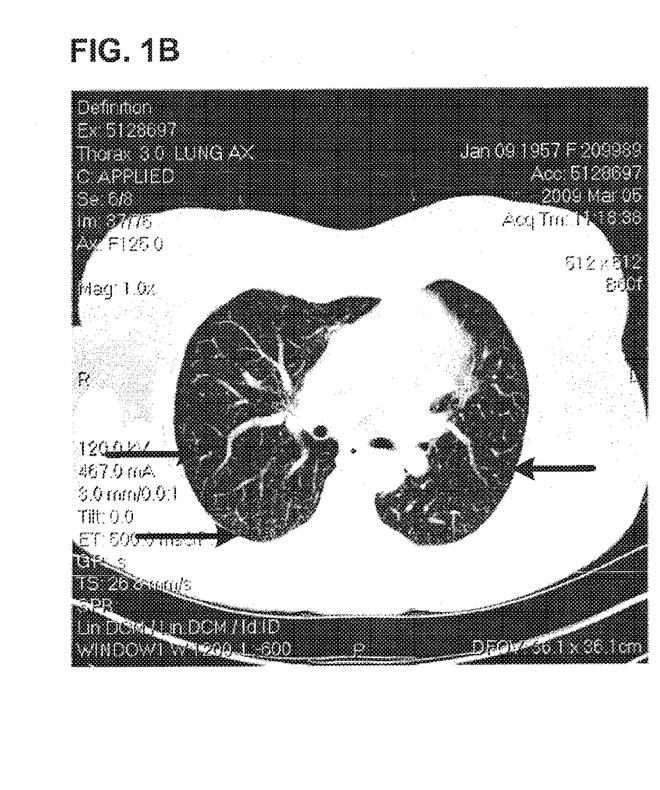
Figure 2A:
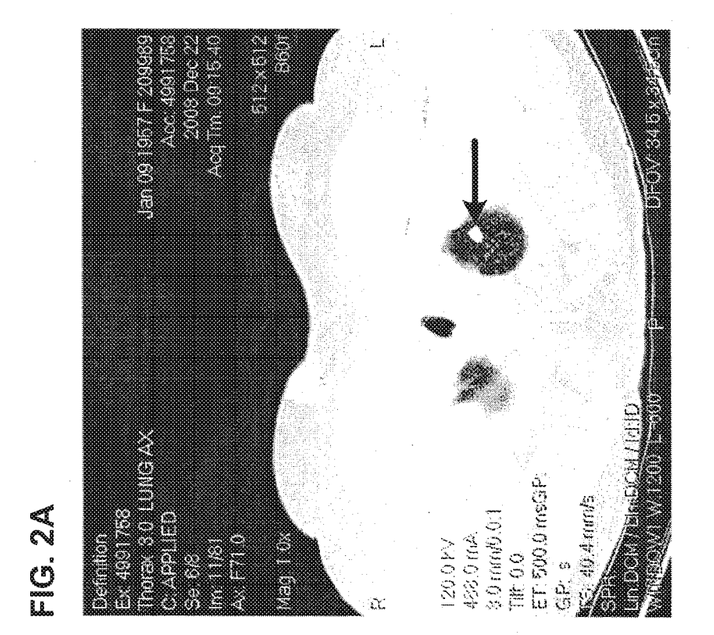
FIGS. 2A and 2B are representations of a CT scan of a lung metastasis from a primary cholangiocarcinoma from a patient unresponsive to previous treatment with a taxane-based drug.
Figure 2B:
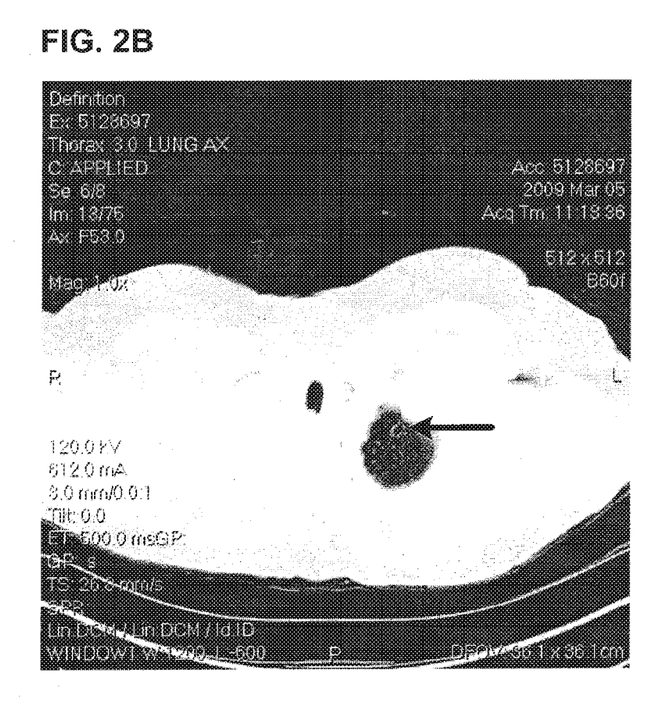
Figure 3A:
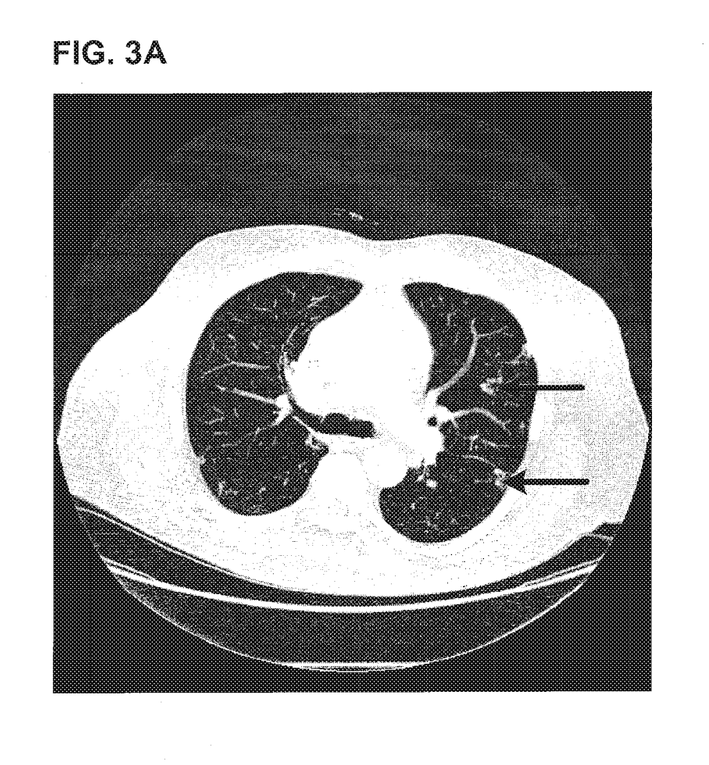
FIGS. 3A and 3B are is a representations of a CT scan of a TCC urothelium in a patient unresponsive to previous treatment with a taxane-based drug.
Figure 3B:
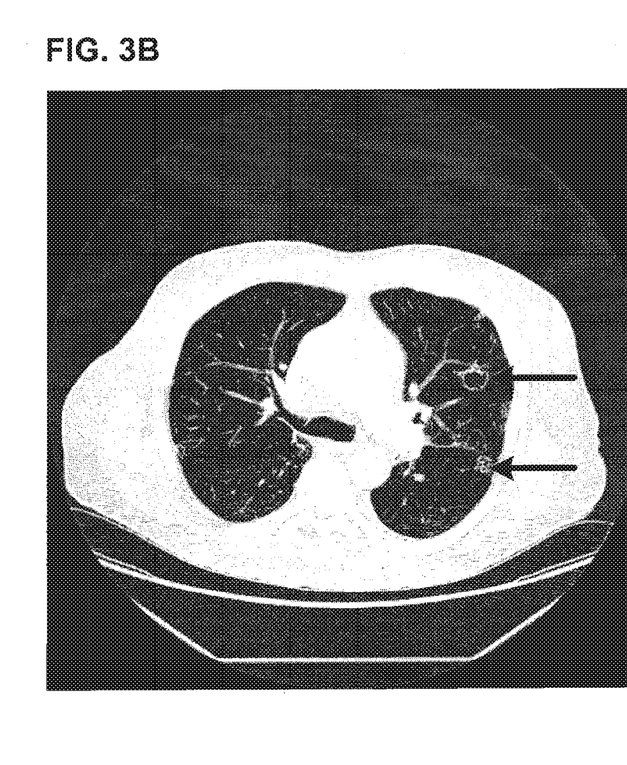
Figure 4A:
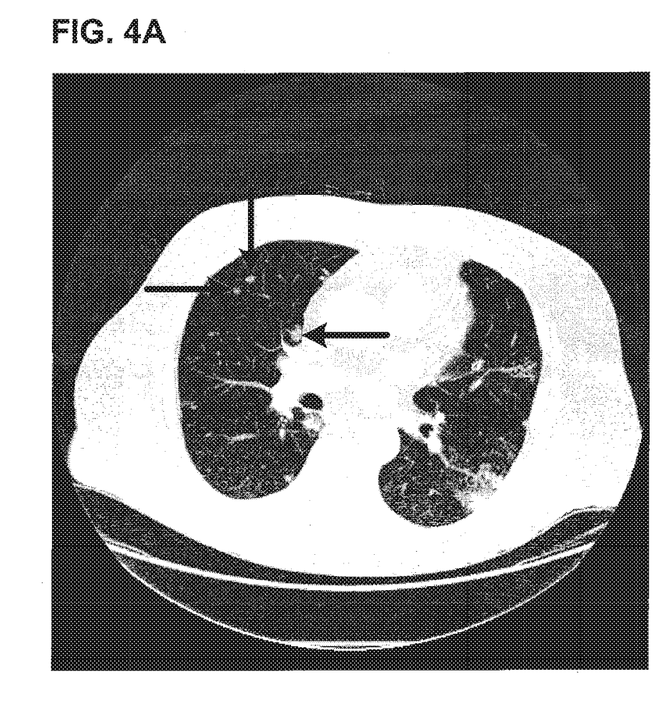
Figure 4B:
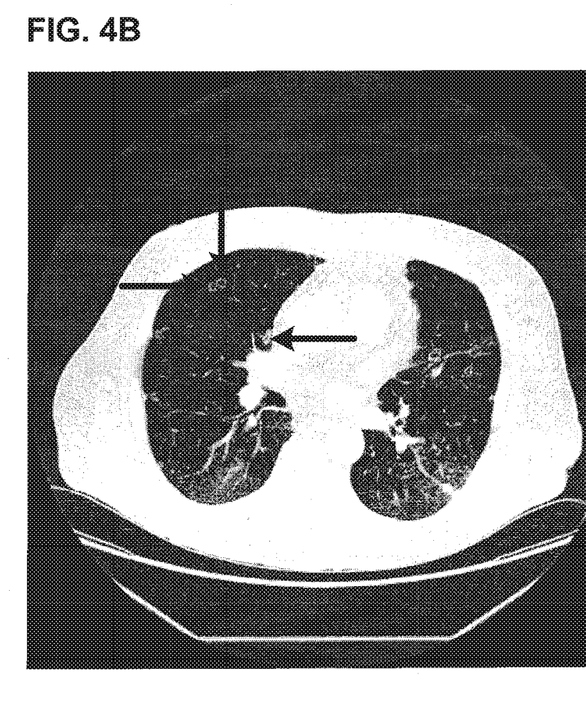

Throughout this application, various patents, patent applications, and publications are referenced. The disclosures of these patents, patent applications, and publications in their entireties are hereby incorporated by reference into this application in order to more fully describe the state of the art as known to those skilled therein as of the date of the invention described and claimed herein. The instant disclosure will govern in the instance that there is any inconsistency between the patents, patent applications, and publications and this disclosure.

Definitions

For convenience, certain terms employed in the specification, examples, and appended claims are collected here. Unless defined otherwise, all technical and scientific terms used herein have the same meaning as commonly understood by one of ordinary skill in the art to which this invention belongs. The initial definition provided for a group or term herein applies to that group or term throughout the present specification individually or as part of another group, unless otherwise indicated.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein.

The term "or" is used herein to mean, and is used interchangeably with, the term "and/or," unless context clearly indicates otherwise.

As used herein, the terms "treat", "treatment" and "contributing to the treatment of" shall mean preventing, retarding the progression or growth of, shrinking, or eliminating a cancer including a solid tumor. As such, these terms include both medical therapeutic and/or prophylactic administration, as appropriate.

As used herein, the term "substantially simultaneously" shall mean that two pharmaceutical preparations (i.e. an $ET_B$ receptor agonist and a chemotherapeutic agent) are administered at the same time. According to this definition, "same time" should be read to include exactly simultaneously as well as within about ten minutes.

The term "about" is used herein to mean a value − or +20% of a given numerical value. Thus, "about 60%" means a value of between 60−(20% of 60) and 60+(20% of 60) (i.e., between 48 and 70).

The term "subject", as used herein, means any subject for whom diagnosis, prognosis, or therapy is desired. For example, a subject can be a mammal, e.g., a human or non-human primate (such as an ape, monkey, orangutan, or chimpanzee), a dog, cat, guinea pig, rabbit, rat, mouse, horse, cattle, or cow.

A "therapeutically effective amount" as used herein means an amount effective to prevent development or growth of, to eliminate, to retard the progression of, or to reduce the size of, a solid tumor. Determination of a therapeutically effective amount is well within the capability of those skilled in the art, especially in light of the detailed disclosure provided herein.

In reference to an $ET_B$ receptor agonist, a "therapeutically effective amount" refers to that amount which is effective to dilate the blood vessels of a tumor. Toxicity and therapeutic efficacy of the $ET_B$ receptor agonist and the chemotherapeutic agent can be determined by standard pharmaceutical procedures in cell cultures or experimental animals, e.g., determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. A high therapeutic index is preferred. The data obtained can be used in formulating a range of dosage for use in humans. The dosage of the active ingredients lies within a range of circulating concentrations that include the $ED_{50}$ with little or no toxicity. The dosage can vary within this range depending upon the dosage form employed, and the route of administration utilized.

General

The present disclosure relates to treatment of metastatic carcinomas and certain primary carcinomas by targeted delivery of a chemotherapeutic agent using an $ET_B$ receptor agonist. $ET_B$ receptor agonists selectively increase blood supply to solid tumors thus increasing delivery of chemotherapeutic agents to a carcinoma being treated. Targeted delivery of chemotherapeutic agents to tumors has the advantage of enhancing the benefit of chemotherapeutic agents while minimizing their systemic toxic effects. Such targeted delivery also serves to lower the required dose of chemotherapeutic agents thus potentially reducing unacceptable adverse effects of these agents.

The targeted delivery of chemotherapeutic agents according to the disclosure utilizes the distinctive features of tumor vasculature. Tumors greater than a few millimeters in size require a constant nutrient supply, and accordingly, develop their own vascular bed and blood flow. Without constant nourishment from these developing blood vessels, the tumors become hypoxic and subsequently die. During angiogenesis, tumor blood vessels develop substantially differently from normal vasculature, and have different properties. Single layered epithelial cells are the first hastily formed tumor blood vessels. These newly formed tumor blood vessels do not have a smooth muscle layer or innervation. Tumors also incorporate mature blood vessels that possess all their autoregulatory functions.

Vascular tone, or the degree to which blood vessels are dilated or constricted, is governed by a host of endogenous factors (including $H^+$, $K^+$, $Ca^{2+}$, $pO_2$, $pCO_2$ and NO), as well as other regulatory substances such as endothelins. Endothelins are a family of cyclic peptides which bind to two distinct surface receptors $ET_A$ and $ET_B$. These receptors mediate biological responses from a variety of stimuli, including vasoactive polypeptides, growth factors, and hormones. $ET_B$ receptors have been found in, without limitation, ovarian cancers, Kaposi's tumor, breast carcinoma, and melanomas. Their increased expression, along with endothelins, has been found in solid tumors. Stimulation of $ET_B$ receptors can cause an increase in blood supply to tumors through vasodilation of tumor blood vessels.

Herein, $ET_B$ receptor agonists can be used to selectively increase blood flow to tumors to enhance the targeted delivery of chemotherapeutic agents. While not being held to any particular theory, it is thought that endothelin agonists stimulate $ET_B$ receptors to dilate tumor blood vessels, thereby increasing blood flow and the resultant delivery of chemotherapeutic agents to the tumor. The increased blood perfusion of tumors caused by endothelin agonists also increases oxygenation of the tissue. Improved oxygenation can enhance the therapeutic action of chemotherapeutic agents. Endothelin also can have mitogenic properties. The mitogenic actions of endothelin can help increase the action of chemotherapeutic agents, when administered together. The mitogenic action of an endothelin agonist can increase the action of chemotherapeutic agents by improving their incorporation into dividing cells, thus increasing their efficacy.

Cancers that are treated with the methods of the disclosure include solid primary and metastatic cholangiocarcinomas and transition cell urothelial carcinomas. The present methods are also effective in treating metastatic carcinomas such as, without limitation, ovarian, gastrointestinal (including colon), breast, prostate, and liver tumors. Additionally, the present methods treat primary and metastatic chemotherapy-resistant cancers such as taxane-resistant prostate, breast, and ovarian cancers. Other cancers at least partially resistant to at least one of YM 155 (surviving inhibitor), AMG-820, gemcitabine, cisplatin, fluorouracil, fp-103, lupron, EDC-3263, FP-1039, taxol, carboplatin, and/or CP873,890 can also be treated by the methods of the disclosure.

Useful $ET_B$ receptor agonists according to the present method include, but are not limited to, one or more of IRL-1620, ET-1, ET-2, ET-3, BQ3020, sarafotoxin S6c, [Ala$^{1,3,11,15}$]ET-1, and combinations thereof.

One useful $ET_B$ receptor agonist is IRL-1620 or N-Succunyl-[Glu$^9$, Ala$^{11,15}$] Endothelin-1 (8-21). A 14 amino acid peptide succinylated at its amino end, IRL-1620 has an amino acid sequence of Suc-Asp-Glu-Glu-Ala-Val-Tyr-Phe-Ala-His-Leu-Asp-Ile-Ile-Trp-OH (SEQ ID NO: 1). It is an analog of ET-1 and binds specifically to $ET_B$ receptors 120,000 times more selectively than it binds to endothelin A receptors.

Useful chemotherapeutic agents include, without limitation, one or more of docetaxel, alkylating agents, antimetabolites, hormones and antagonists thereof, radioisotopes, antibodies, as well as natural products, and combinations thereof. For example, an $ET_B$ receptor agonist can be administered with antibiotics, such as doxorubicin and other anthracycline analogs, nitrogen mustards, such as, without limitation, cyclophosphamide, pyrimidine analogs such as, without limitation, 5-fluorouracil, cisplatin, hydroxyurea, and its natural and synthetic derivatives, and the like. As another example, in the case of mixed tumors, such as adenocarcinoma of the breast, where the tumors include gonadotropin-dependent and gonadotropin-independent cells, the $ET_B$ receptor agonist can be administered in conjunction with, without limitation, leuprolide or goserelin (synthetic peptide analogs of LH-RH). Additional non-limiting examples of chemotherapeutic agents that can be used with the present invention include adriamycin, camptothecin, carboplatin, cisplatin, daunorubicin, doxorubicin, interferon (alpha, beta, and/or gamma), interleukin 2, irinotecan, paclitaxel, topotecan, and therapeutically effective analogs, combinations, and derivatives of the same.

Pharmaceutical Compositions and Administration

The dose of $ET_B$ receptor agonist and of the chemotherapeutic agent depends on the agonist and agent being used and the patient being treated. The exact formulation and dosage can be determined by an individual physician in view of the patient's condition. Dosage amount and interval can be adjusted individually to provide levels of the active ingredients that are sufficient to maintain therapeutic or prophylactic effects. For example, the amount of pharmaceutical composition administered can be dependent on the subject being treated, on the subject's weight, the severity of the affliction, the manner of administration, and the judgment of the prescribing physician.

The $ET_B$ receptor agonist and the chemotherapeutic agent can be administered alone, or in admixture with a pharmaceutically acceptable carrier or excipient selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of the active ingredients into preparations which can be used pharmaceutically.

As used herein, a "pharmaceutically acceptable carrier" means a carrier that can be administered to a subject together with an $ET_B$ receptor agonist and/or chemotherapeutic agent described herein, which does not destroy the pharmacological activity thereof. Pharmaceutically acceptable carriers include, e.g., solvents, dispersion media, coatings, antibacterial and antifungal agents, isotonic and absorption delaying agents, and the like, compatible with pharmaceutical administration. Supplementary active compounds can also be incorporated into the compositions.

Non-limiting examples of pharmaceutically acceptable carriers that can be used include poly(ethylene-co-vinyl acetate), PVA, partially hydrolyzed poly(ethylene-co-vinyl acetate), poly(ethylene-co-vinyl acetate-co-vinyl alcohol), a cross-linked poly(ethylene-co-vinyl acetate), a cross-linked partially hydrolyzed poly(ethylene-co-vinyl acetate), a cross-linked poly(ethylene-co-vinyl acetate-co-vinyl alcohol), poly-D, L-lactic acid, poly-L-lactic acid, polyglycolic acid, PGA, copolymers of lactic acid and glycolic acid (PLGA), polycaprolactone, polyvalerolactone, poly (anhydrides), copolymers of polycaprolactone with polyethylene glycol, copolymers of polylactic acid with polyethylene glycol, polyethylene glycol; and combinations and blends thereof.

Other carriers include, e.g., aqueous gelatin, aqueous protein, a polymeric carrier, a cross-linking agent, or a combination thereof. In another instances, the carrier can be a matrix. In yet other instances, the carrier includes water, a pharmaceutically acceptable buffer salt, a pharmaceutically acceptable buffer solution, a pharmaceutically acceptable antioxidant, ascorbic acid, one or more low molecular weight pharmaceutically acceptable polypeptides, a peptide comprising about 2 to about 10 amino acid residues, one or more pharmaceutically acceptable proteins, one or more pharmaceutically acceptable amino acids, an essential-to-humans amino acid, one or more pharmaceutically acceptable carbohydrates, one or more pharmaceutically acceptable carbohydrate-derived materials, a non-reducing sugar, glucose, sucrose, sorbitol, trehalose, mannitol, maltodextrin, dextrins, cyclodextrin, a pharmaceutically acceptable chelating agent, EDTA, DTPA, a chelating agent for a divalent metal ion, a chelating agent for a trivalent metal ion, glutathione, pharmaceutically acceptable nonspecific serum albumin, and/or combinations thereof.

A pharmaceutical composition containing an $ET_B$ receptor agonist and/or a chemotherapeutic agent can be formulated to be compatible with its intended route of administration as known by those of ordinary skill in the art. Non-limiting examples of routes of administration include parenteral, intravenous, intradermal, subcutaneous, oral (e.g., inhalation), transdermal (topical), transmucosal, vaginal and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, polyethoxylated castor oil, CREMOPHOR® EL (BASF, Parsippany, N.J.) or phosphate buffered saline (PBS). In all cases, the composition should be sterile and should be fluid to the extent that easy syringability exists. The composition should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. It may be desirable to include isotonic agents, for example, sugars, polyalcohols such as mannitol, sorbitol, or sodium chloride in the composition. Prolonged absorption of the injectable compositions can be accomplished by including in the composition an agent that delays absorption, for example, aluminum monostearate and gelatin (see, e.g., *Remington: The Science and Practice of Pharmacy*, 21st edition, Lippincott Williams & Wilkins, Gennaro, ed. (2006)).

Sterile injectable solutions can be prepared by incorporating an $ET_B$ receptor agonist and/or a chemotherapeutic agent in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the methods of preparation include, without limitation, vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, an $ET_B$ receptor agonist and/or chemotherapeutic agent can be incorporated with excipients and used in the form of tablets, pills, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, an $ET_B$ receptor agonist and/or a chemotherapeutic agent can be delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, but are not limited to, for example, for transmucosal administration, detergents, bile salts, and fusidic acid derivatives. Transmucosal administration can be accomplished through the use of nasal sprays or suppositories. For transdermal administration, the active compounds are formulated into, e.g., ointments, salves, gels, or creams as generally known in the art.

The pharmaceutical compositions containing an $ET_B$ receptor agonist and/or a chemotherapeutic agent can also be prepared in the form of suppositories (e.g., with conventional suppository bases such as cocoa butter and other glycerides) or retention enemas for rectal delivery.

Some pharmaceutical compositions can be prepared with a carrier that protects the $ET_B$ receptor agonist and/or the chemotherapeutic agent against rapid elimination from the body, such as a controlled release formulation, including implants and microencapsulated delivery systems (as described, e.g., in Tan et al., *Pharm. Res.* 24:2297-2308, 2007). Biodegradable, biocompatible polymers can be used, such as ethylene vinyl acetate, polyanhydrides, polyglycolic acid, collagen, polyorthoesters, and polylactic acid. Methods for preparation of such formulations are apparent to those skilled in the art. The materials can also be obtained commercially (e.g., from Alza Corp., Mountain View, Calif.). Liposomal suspensions (including liposomes with the $ET_B$ receptor agonist and/or the chemotherapeutic agent on their surface) can also be used as pharmaceutically acceptable carriers. These can be prepared according to methods known to those skilled in the art, e.g., as described in U.S. Pat. No. 4,522,811.

It may be advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of the $ET_B$ receptor agonist and/or the chemotherapeutic agent such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. While compounds that exhibit toxic side effects can be used, care should be taken to design a delivery system that targets such compounds to the site of affected tissue in order to minimize potential damage to uninfected cells and, thereby, reduce side effects. For example, a dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography. Information for preparing and testing such compositions are known in the art (see, e.g., *Remington's The Science and Practice of Pharmacy*, 21st edition, Lippincott Williams & Wilkins, Gennaro, ed. (2006)).

The data obtained from cell culture assays and animal studies can be used in formulating a range of dosage for use in humans. The dosage of such compounds lies generally within a range of circulating concentrations that include the $ED_{50}$ with little or no toxicity. The dosage can vary within this range depending upon the dosage form employed and the route of administration utilized. For any compound described herein, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography. Information for preparing and testing such compositions are known in the art (see, e.g., *Remington's The Science and Practice of Pharmacy*, 21st edition, Lippincott Williams & Wilkins, Gennaro, ed. (2006)).

A therapeutically effective amount of a chemotherapeutic agent depends, in part, on the patient, the cancer to be treated and the route of administration. In some instances, a therapeutically effective amount or dosage of a chemotherapeutic agent can range from about 0.001 mg/kg body weight to about 100 mg/kg body weight, e.g., from about 0.01 mg/kg body weight to about 50 mg/kg body weight, from about 0.025 mg/kg body weight to about 25 mg/kg body weight, from about 0.1 mg/kg body weight to about 20 mg/kg body weight, from about 0.25 mg/kg body weight to about 20 mg/kg body weight, from about 0.5 mg/kg body weight to about 20 mg/kg body weight, from about 0.5 mg/kg body weight to about 10 mg/kg body weight, from about 1 mg/kg body weight to about 10 mg/kg body weight, or about 5 mg/kg body weight. Dosages can also be in mg/m$^2$ a dosing unit used for many chemotherapy drugs based on body surface area (BSA), i.e., mg per body surface area of patient. In a specific example, a therapeutically effective dose of docetaxel is from about 60 mg/m$^2$ to about 75 mg/m$^2$.

Likewise, a therapeutically effective amount of $ET_B$ receptor agonist depends, in part, on the patient, the cancer to be treated and the route of administration. The dose of $ET_B$ receptor agonist administered is an amount effective to dilate the blood vessels of the tumor to be treated. For example, in some non-limiting instances, therapeutically effective amounts of intravenously administered IRL-1620 are about 0.5 µg/m$^2$, about 1 µg/m$^2$ to about 12 µg/m$^2$, from about 5 µg/m$^2$ to about 11 µg/m$^2$, or about 11 µg/m$^2$. In one example, the maximum tolerated dosage of IRL-1620 in combination with docetaxel is 11 µg/m$^2$. In one example, the maximum tolerated dosage of IRL-1620 in combination with docetaxel is 15.1 µg/m$^2$.

A physician will appreciate that certain factors may influence the dosage required to effectively treat a subject, including but not limited to the severity of the cancer, previous treatments, the general health and/or age of the subject, and other diseases present. It will also be appreciated that the effective dosage of an $ET_B$ receptor agonist and/or a chemotherapeutic agent used for treatment may increase or decrease over the course of a particular treatment.

Treatment of a subject with a therapeutically effective amount of $ET_B$ receptor agonist depends, in part, on the patient, the cancer to be treated and the route of administration and/or a chemotherapeutic agent-containing pharmaceutical composition described herein can be a single treatment, continuous treatment, or a series of treatments divided into multiple doses. The treatment can include a single administration, continuous administration, or periodic administration over one or more years. Chronic, long-term administration can be indicated in many cases. In some instances, a subject is treated for up to two years, for up to 1.5 years, or for up to one year. In other instances, a subject is treated for up to 74 weeks. In other instances, a subject is treated for up to 6 months. In particular instances, a subject is treated from about 40 to about 75 weeks. In some embodiments, the subject is treated for a bout 20 to about 40 weeks, or from 20 to about 74 weeks, or for 20, 25, 30, 35, 40, 45, 50, 55, 60, 65, 70, 75, 80, 85, 90, 95, or 100 weeks. In yet another situation, a subject is treated for up to 100 days. In some examples, a subject is treated with IRL-1620 and docetaxel in a time frame of one time per week for up to 10 weeks, or alternatively between 2 weeks to 8 weeks, between about 3 weeks to 7 weeks, or for about 4 weeks, 5 weeks, 6 weeks, 10 week to 80 weeks, 20 weeks to 40 weeks, or 40 weeks to 74 weeks In other instances, a subject can be treated substantially continuously for the same amounts of time listed above. In other situations, a subject can be treated once per day, twice per day, once per week, or once per month.

The $ET_B$ receptor agonist and the chemotherapeutic agent can be administered substantially simultaneously or can be administered sequentially (with the chemotherapeutic agent administered prior to the $ET_B$ receptor agonist or the $ET_B$ receptor agonist administered prior to the chemotherapeutic agent). In certain non-limiting examples where the $ET_B$ receptor agonist and the chemotherapeutic agent are administered substantially simultaneously, they can be administered as a single composition.

Aspects of the present specification disclose, in part, a kit comprising components useful in performing any of the methods disclosed herein. In one embodiment, a kit comprises an $ET_B$ receptor agonist and a chemotherapeutic agent.

Instructions as disclosed herein may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, tape, or CD., on which the information has been recorded. Yet another means that may be present is a website address which may be used via the internet to access the information at a removed site. Any convenient means may be present in the kits.

For veterinary use, the active ingredients are administered as a suitably acceptable formulation in accordance with normal veterinary practice. The veterinarian can readily determine the dosing regimen that is most appropriate for a particular animal.

EXAMPLES

Reference will now be made to specific examples illustrating the disclosure. It is to be understood that the examples are provided to illustrate preferred embodiments and that no limitation to the scope of the disclosure is intended thereby.

Example 1

IRL-1620 and Docetaxel Treatment of Carcinoma

This study was a 2-part, open label, single arm, dose escalation study of the $ET_B$ receptor agonist, IRL-1620 in combination with the chemotherapeutic agent, docetaxel.

Part 1 of the study defined maximum toxic dosage (MTD), optimal dose of IRL-1620, and measured PK/PD profiles.

Patients with progressive or recurrent carcinoma who failed all standard therapies were eligible for the study. Patients with a history of CHF, stroke, symptomatic COPD, ventricular arrhythmia were excluded from the study. 30 patients were enrolled in part 1 of the study. Patient characteristics were as follows. 14 men and 16 women with a median age of 61 years (range 41-77) took part in the study. 9 patients had prostate cancer, 3 had breast cancer, 4 had female reproductive malignancies (ovarian, cervical, or endometrial cancers), 3 had GI-related malignancies (cholangiocarcinoma, esophageal or gastric cancers), 2 had pancreatic cancers, and 9 had omental, lung, adenocortical, anal, neuroendocrine, soft tissue sarcoma, or renal cancers.

Eligible patients received IRL-1620 delivered intravenously over one minute on Days 1, 8 and 15. On Day 8 patients underwent a series of four $H_2^{15}O$ PET Blood Flow (BF) scans to assess alterations in BF induced by IRL-1620 in tumor and non-tumor regions. Fifteen minutes after receiving IRL-1620 on Day 15, patients received docetaxel, 60 mg/m$^2$, administered by infusion over 1 hour.

Part 2 of the study focuses on the safety and tolerability of docetaxel administered at a dose of 75 mg/m$^2$ following IRL-1620 at MTD and an additional dose in 2 groups. CT or MRI scans are used to assess the patient's tumor size. A series of dynamic contrast enhancer pattern MRI scans are used to measure any increases in blood flow induced by IRL 1620.

IRL-1620 dose levels administered were 0.5 µg/m$^2$ (n=1), 1.0 µg/m$^2$ (n=1), 2.0 µg/m$^2$ (n=3), 2.8 µg/m$^2$ (n=3), 3.7 µg/m$^2$ (n=1), 3.9 µg/m$^2$ (n=4), 5.5 µg/m$^2$ (n=3), 7.7 µg/m$^2$ (n=3), 10.8 µg/m$^2$ (n=4), 15.1 µg/m$^2$ (n=3), 10.8 µg/m$^2$ (n=4). The docetaxel dose level was 60 mg/m$^2$ or 75 mg/m$^2$.

Dose limiting toxicities were observed at a dose of 15.1 µg/m$^2$ of IRL-1620. Maximum tolerated dose was defined as 11 µg/m$^2$. Drug related serious adverse events were (n; %): ischemic stroke (1, 0.03), dyspnea (1, 0.03), pleural effusion (1, 0.03). Disease progression was the most common reason for the discontinuation of the study (84%).

There were 5 cases of stable disease (16% SD). Prolonged clinical benefit was observed in 4 cases (13%) where patients stayed on the study for 20-74 weeks. A PSA response in previously docetaxel treated prostate cancer patient as well as a measurable decrease in metastatic prostate cancer. Anti-tumor activity was seen in patients with docetaxel-pretreated patients. One patient with cholangiocarcinoma achieved complete regression of lung metastasis within 3 months of treatment and stayed on the study for 41 weeks before eventually progressing. Treatment with IRL-1620 did not result in any measurable changes in blood flow.

EQUIVALENTS

Those skilled in the art will recognize, or be able to ascertain, using no more than routine experimentation, numerous equivalents to the specific composition and procedures described herein. Such equivalents are considered to be within the scope of this invention, and are covered by the following claims.

What is claimed is:

1. A method of treating a metastatic chemotherapy-resistant cancer, wherein said cancer comprises tumors comprising blood vessels expressing $ET_B$ receptors, said method comprising: administering a therapeutically effective amount of an endothelin B ($ET_B$) receptor agonist and a therapeutically effective amount of chemotherapeutic agent to a subject suffering from a chemotherapy-resistant cancer; wherein the $ET_B$ receptor agonist is IRL-1620 and wherein administration results in a reduction in the size or in the growth of the chemotherapy-resistant cancer, thereby treating the chemotherapy-resistant cancer.

2. The method of claim 1, wherein the therapeutically effective amount of IRL-1620 is about 5 μg/m$^2$ to about 11 μg/m$^2$.

3. The method of claim 1, wherein the chemotherapeutic agent is a docetaxel.

4. The method of claim 1, wherein the chemotherapy resistant cancer being treated is a prostate, breast, or ovarian cancer.

5. The method of claim 1, wherein the cancer being treated is unresponsive to prior taxane chemotherapy.

6. The method of claim 3, wherein the therapeutically effective amount of docetaxel is about 60 mg/m$^2$ to about 75 mg/m$^2$.

7. The method of claim 3, wherein the therapeutically effective amount of docetaxel is about 60 mg/m$^2$.

8. The method of claim 1, wherein the $ET_B$ receptor agonist and the chemotherapeutic agent are administered substantially simultaneously.

9. The method of claim 4, wherein the chemotherapy-resistant cancer being treated is a prostate cancer.

10. The method of claim 4, wherein the chemotherapy-resistant cancer being treated is a breast cancer.

11. The method of claim 4, wherein the chemotherapy-resistant cancer being treated is an ovarian cancer.

\* \* \* \* \*

SEQUENCE LISTING

```
<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: ETB receptor agonist IRL-1620
<220> FEATURE:
<221> NAME/KEY: MOD_RES
<222> LOCATION: (1)..(1)
<223> OTHER INFORMATION: Succinylated

<400> SEQUENCE: 1

Asp Glu Glu Ala Val Tyr Phe Ala His Leu Asp Ile Ile Trp
1               5                   10
```